US00PP13857P39

(12) United States Plant Patent
Boeder

(10) Patent No.: US PP13,857 P3
(45) Date of Patent: Jun. 3, 2003

(54) CHRYSANTHEMUM PLANT NAMED 'MIDAS TIME GOLD'

(75) Inventor: Mark Roland Boeder, West Wittering (GB)

(73) Assignee: Cleangro Limited (GB)

( * ) Notice: Subject to any disclaimer, the term of this patent is extended or adjusted under 35 U.S.C. 154(b) by 232 days.

(21) Appl. No.: 09/768,038

(22) Filed: Jan. 22, 2001

(65) Prior Publication Data

US 2002/0100096 P1 Jul. 25, 2002

(51) Int. Cl.[7] ..... A01H 5/00

(52) U.S. Cl. ..... Plt./296

(58) Field of Search ..... Plt./296, 295

(56) References Cited

U.S. PATENT DOCUMENTS

PP7,469 P 3/1991 Vandenberg ..... Plt./295

*Primary Examiner*—Kent L. Bell
(74) *Attorney, Agent, or Firm*—Howrey Simon Arnold & White, LLP

(57) ABSTRACT

A new variety of Chrysanthemum plant named 'Midas Time Gold,' having golden-yellow quilled/spoon shaped ray florets with dark green disc florets.

1 Drawing Sheet

LATIN NAME OF THE GENUS AND SPECIES

Botanical classification: *Dendranthema grandiflora.*

VARIETY DENOMINATION

The new Chrysanthemum variety denomination is 'Midas Time Gold'.

BACKGROUND OF THE INVENTION

The present invention comprises a new and distinct cultivar of Chrysanthemum botanically known as *Dendranthema grandiflora*, and referred to by the cultivar name 'Midas Time Gold.'

'Midas Time Gold,' identified as MTG1, originated from a spontaneous whole plant mutation found by Mark Boeder in a controlled cultivated planting in Chichester, West Sussex, United Kingdom of the variety known as 'Midas Time Yellow.' The parent plant, 'Midas Time Yellow,' is an undistributed, unpatented variety. The new variety 'Midas Time Gold' has been asexually reproduced by vegetative stemcuttings in Leythorne Nursery, Chichester, West Sussex, United Kingdom and the distinguishing characteristics are retained through successive generations of asexual reproduction.

BRIEF SUMMARY OF THE INVENTION

'Midas Time Gold' is a pot type of Chrysanthemum plant variety having golden-yellow ray florets with quilled and spoon shaped tips and a single flower type.

Comparison with Parent

Plants of the new Chrysanthemum variety 'Midas Time Gold' are similar to the parent cultivar 'Midas Time Yellow' in plant habitat and growth rate. In side-by-side comparisons in Chichester, West Sussex, United Kingdom, under commercial practice, plants of the new Chrysanthemum variety 'Midas Time Gold' produced golden-yellow ray florets whereas the parent cultivar 'Midas Time Yellow' produced yellow flowers.

Comparison with Other Varieties

Plants of the new Chrysanthemum variety 'Midas Time Gold' are dissimilar to the cultivar 'Miramar,' U.S. Plant Pat. No. 7,469, in plant habitat and growth rate. In side-by-side comparisons in Chichester, West Sussex, United Kingdom, under commercial practice, plants of the new Chrysanthemum variety 'Midas Time Gold' differed from plants of the cultivar 'Miramar' in at least the following characteristics:

1. The new variety 'Midas Time Gold' produced golden-yellow flowers whereas the cultivar 'Miramar' produced yellow flowers.
2. Plants of the new variety 'Midas Time Gold' have a smaller and shorter inflorescence than plants of the cultivar 'Miramar'.
3. Plants of the new variety 'Midas Time Gold' have spoon/quill shaped ray florets whereas plants of the cultivar 'Miramar' have flat ray florets.

BRIEF DESCRIPTION OF ILLUSTRATIONS

Typical plant and flowers for the new Chrysanthemum variety 'Midas Time Gold' are shown in the accompanying scanned image printed from a digital photograph. The colors shown are as true as possible within the usual limits of this kind of illustration. FIG. 1 is a whole plant view of the new variety 'Midas Time Gold' grown in a pot. The plant shown in the illustration and described herein is 53 days after the commencement of Short Days.

DETAILED BOTANICAL DESCRIPTION

The following description of the new Chrysanthemum variety 'Midas Time Gold' is of plants grown in a greenhouse at Leythorne Nursery, Chichester, United Kingdom in the month of November. The cultivar has not been observed under all possible environmental conditions. The phenotype may vary significantly with variations in the environment such as temperature, length of day and light intensity, without any variance in genotype. The commercial classification of the new variety is a pot Chrysanthemum.

Plants of the new variety have been grown successfully under temperature conditions averaging about 18° C. at night and about 20° C. to 24° C. during the day under light conditions of about 5000 to 6000 foot candles. The plants respond well to the use of growth retardant, such as one B9 treatment at about 2 g/liter. To produce a commercial product the plants may be pinched once with the center bud removed. The typical container size for commercial growth is 1 liter. It has been observed that the shelf life of the new variety is about 21 days with a response time of about 7.5 weeks.

The new variety may be produced as a pot Chrysanthemum. The following description is with respect to a plant produced as a pot Chrysanthemum. In the description of this new Chrysanthemum variety, color values have been taken from The Royal Horticultural Society Colour Chart (R.H.S.C.C.).

Plant

Plant type: Pot chrysanthemum.
Habit: Upright.
Height: 20–25 cm.
Width: 35 cm.
Branching characteristics: Upright spreading.
Length of lateral branches: 15–17 cm.
Number of breaks from pinch: 4–5.
Stem color: Near 137C.
Response time: 7.5 weeks.
Vigor: Short to very short.
Shelf life: Near 21 days.
Disease/pest susceptibility/resistance: None observed to date.
Growth retardant type and treatment: 1 application of 2 gram/liter B9, 2, 21, and 28 days after sticking unrooted cuttings. The plants were grown for 2 weeks in Long Day conditions (20 hrs. light) and then transferred to Short Day conditions (13 hrs. dark).
Propagation:
*Type.*—Unrooted cuttings in pot under plastic sheet.
*Time to rooting.*—14 days with soil temperatures of 21° C.
*Rooting habit.*—Evenly distributed over pot.

Foliage

Number of leaves per lateral branch: 7–9.
Compound or single: Single.
Arrangement of leaves: Alternate. Shape of Leaf: typical 5 lobed, ovate. Size of Leaf: Width (cm): 0–5.0. Length (cm): 0–10.0. Leaf Apex: mucronate. Base: cordate. Attachment: petioled. Aspect: slight undulating. Margin: Entire, palmately lobed. Surface characteristics: Top: pubescent. Bottom: pubescent.
Petiole: Color: near 137B. Length: 0–2.5 cm.
Venation: 1 prominent midvein, 4–6 well developed side veins. Color: upper side: near 138C. under side: near 138B.
Color: Mature Leaf, upper side: near 139A; under side: near 137C. Young leaf, upper side: near 139A; under side: near 137C.

Inflorescence

Inflorescence: Single flowers with large golden-yellow ray florets having a quill/spoon shaped tip and a dark green center.
Inflorescence type: Single.
Inflorescence shape: Cupped to flat.
Flowering habit: Top-down.
Number of blossoms per branch: 2–4.
Inflorescence form: Cyme. Depth of fully expanded blossoms: 2.5–3.5 cm. Diameter of fully expanded blossoms: 7.0–9.0 cm.
Phyllaries:
*Number.*—25–30.
*Outer surface color.*—Near 137B.
*Inner surface color.*—137D.
*Length.*—0.6–1.1 cm.
*Width.*—0.2–0.6 cm.
*Texture/appearance.*—Pubescent.
Peduncles:
*Length.*—Terminal: 4.0–6.0 cm; lateral: 8.0–10.0 cm.
*Color.*—Near 138A.
*Surface.*—Pubescent.
*Habit.*—Slight undulating.
*Strength.*—Strong.
Ray florets:
*Form/shape.*—Partly quilled/partly spoon shaped in 1 row.
*Texture/appearance.*—Matte.
*Number per flower.*—50–60.
*Length.*—2.5–4.0 cm.
*Width.*—0.3–0.6 cm.
*Apex.*—Rounded.
*Base.*—Tubular.
*Margin.*—Entire.
Disc florets:
*Form/shape.*—Cylindrical.
*Texture/appearance.*—Glossy.
*Number per flower.*—180–220.
*Length.*—0.5–0.8 cm.
*Width.*—0.1–0.2 cm.
*Diameter of disc.*—1.8–2.3 cm.
Fragrance: faint.
Flower bud (at onset of color):
*Length.*—1.3–1.6 cm.
*Diameter.*—1.0–1.4 cm.
*Form/shape.*—Spherical.
General inflorescence color:
1. Ray florets, upper side:
*Immature.*—Near 21A.
*Mature.*—Near 23B.
*Older/fading.*—Near 16B.
2. Ray florets, under side:
*Immature.*—Near 7A.
*Mature.*—Near 12B.
*Older/fading.*—Near 12C.
3. Disc florets:
*Immature.*—Near 137B.
*Mature.*—Near 151B.
*Older/fading.*—Near 151D.
4. Bud: near 147A.

Inflorescence progression with age: dark green center disappears when flowers mature. Some pollen developing in center.

Reproductive Organs

Ray florets: Pistillate
*Pistil number.*—About 5.
*Stigma color.*—Near 2A.
*Stigma shape.*—Forked.
*Style color.*—Near 154B.

*Style length.*—0.2–0.6 cm.

Disc florets: Pistillate

*Pistil number.*—5.

*Stigma color.*—Near 2A.

*Stigma shape.*—Fork.

*Style color.*—Near 154B.

*Style length.*—0.2–0.4 cm.

Staminate:

*Stamen number.*—5.

*Anther shape.*—Thread.

*Anther color.*—Near 14B.

*Pollen color.*—Near 13A.

*Pollen quantity.*—Little.

What is claimed is:

1. A new and distinct variety of Chrysanthemum plant named 'Midas Time Gold' as described and illustrated.

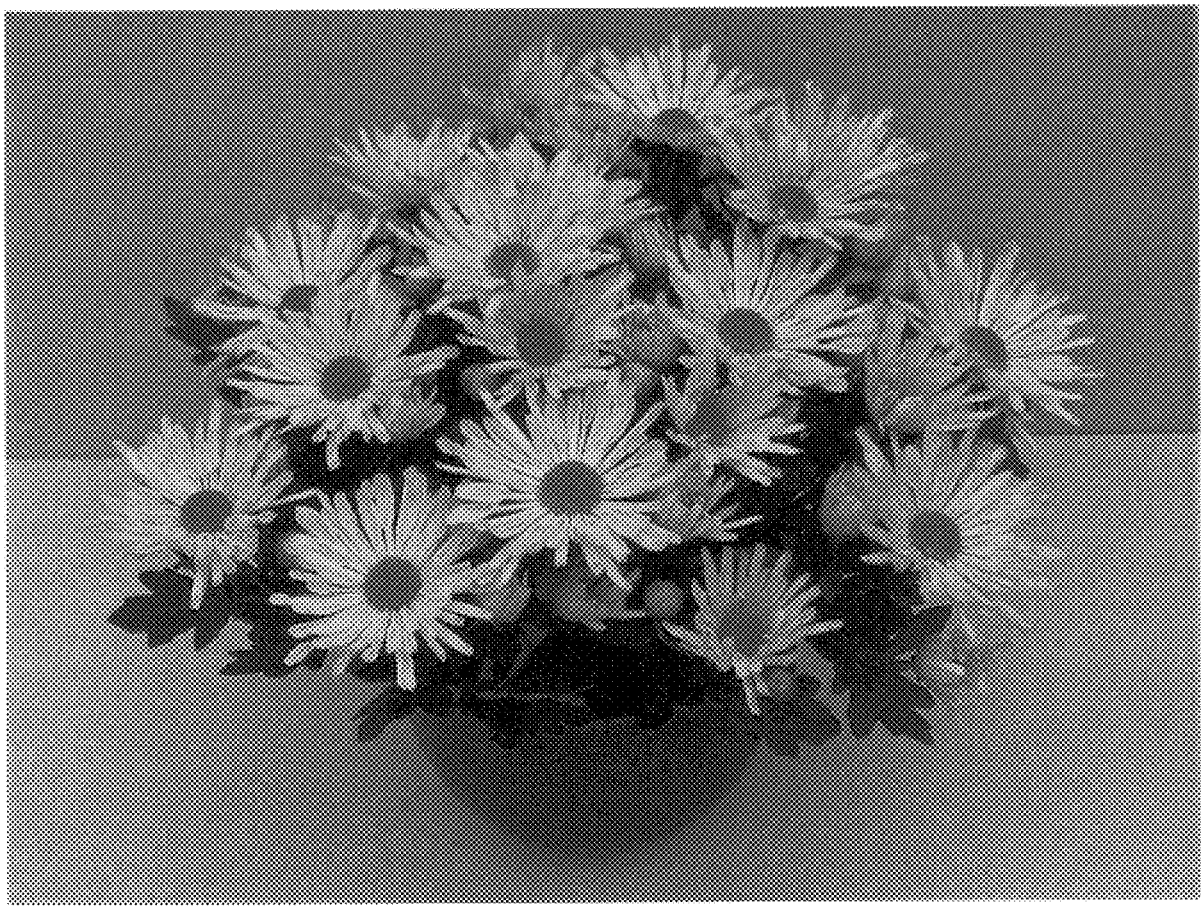

* * * * *